United States Patent [19]

Roffia et al.

[11] Patent Number: 4,794,198
[45] Date of Patent: Dec. 27, 1988

[54] CATALYTIC PROCESS FOR THE MANUFACTURE OF OXIMES

[75] Inventors: Paolo Roffia, Saronno; Mario Padovan, Milan; Giuseppe Leofanti, Bollate; Maria A. Mantegazza, Cambiago; Giordano De Alberti, Besnate; Giorgio R. Tauszik, Milan, all of Italy

[73] Assignee: Montedipe S.p.A., Milan, Italy

[21] Appl. No.: 59,536

[22] Filed: Jun. 8, 1987

[30] Foreign Application Priority Data

Nov. 14, 1986 [IT] Italy ................................ 22346 A/86
Mar. 6, 1987 [IT] Italy ................................ 19607 A/87

[51] Int. Cl.⁴ .......................................... C07C 131/04
[52] U.S. Cl. .................................... 564/267; 564/253; 564/265; 564/266; 564/268
[58] Field of Search ............... 564/253, 265, 266, 267, 564/268

[56] References Cited

U.S. PATENT DOCUMENTS

| | | | |
|---|---|---|---|
| 4,163,756 | 8/1979 | Armor .................................. | 564/253 |
| 4,504,681 | 3/1985 | Armor .................................. | 564/253 |
| 4,560,797 | 12/1985 | Yamanis et al. ..................... | 564/253 |

FOREIGN PATENT DOCUMENTS 208311 1/1987 European Pat. Off. ............ 564/253

*Primary Examiner*—James H. Reamer
*Attorney, Agent, or Firm*—Stevens, Davis, Miller & Mosher

[57] ABSTRACT

The invention concerns a catalytic process for the manufacture of oximes by reaction, in the liquid phase, of the corresponding carbonylic compounds with $NH_3$ and $H_2O_2$, in which process the catalyst is substantially consisting of a crystalline material with a zeolitic structure containing silicon and titanium, subjected, before use, to an activating treatment with $H_2O_2$.

31 Claims, 2 Drawing Sheets

CATALYTIC PROCESS FOR THE MANUFACTURE OF OXIMES

BACKGROUND OF THE INVENTION

It is known, from German Pat. No. 1.245.371, that cyclohexanone-oxime may be obtained by catalytic reaction of cyclohexanone with $NH_3$ and $H_2O_2$, in the liquid phase, at 5°–40° C. and with suitable ratios of the reactants, in the presence of a catalyst consisting of phospho-tungstic acid or of similar compounds; a drawback of this method is, however, that this type of catalyst is difficult to handle, especially during the separation of the product from the catalyst.

European Pat. No. 208311, in the name of the Applicant, teaches that a more convenient alternative to this route may be offered by using, as a catalyst, a crystalline material with a zeolitic structure containing silicon and titanium. The Applicant has now found that a particular activating treatment of such catalyst gives rise to exceptional and altogether surprising catalytic properties.

DISCLOSURE OF THE INVENTION

In its broadest aspect of the invention concerns a catalytic process for the manufacture of oximes by reaction in the liquid phase of the corresponding carbonylic compounds with ammonia and hydrogen peroxide (ammoximation), characterized in that the catalyst is substantially consisting of a crystalline material with a zeolitic structure containing silicon and titanium, subjected, before its use, to an activating treatment with hydrogen peroxide (hereinafter: activation).

Excellent results were achieved by using titanium-silicalites, optionally in admixture with an inert binder; such titanium-silicalites are well known materials, described for instance in British Pat. No. 2.071.071 and in the European Patent Application No. 132550; obviously a titanium-silicalite may be replaced, at least partially, by a zirconium-silicalite or by a hafnium-silicalite.

The titanium-silicalites activated according to the invention were also exploited in many continuous tests, for several hours and even days, without any evidence of decay: in some cases, the yields were even higher, with respect to the corresponding discontinuous test. Best results were obtained in the ammoximation of a carbonylic compound selected from acetone, cyclohexanone, methyl-ethyl-ketone (MEK, namely butan-2-one), acetophenone, cyclododecanone, enanthic aldehyde (1-heptanal) and benzaldehyde.

We list hereinafter some details concerning the different ways in which the invention can be performed, without limiting however in any way the scope of the invention itself. A titanium-silicalite can be prepared, for instance, starting from different sources of titanium (like tetraethyl- or tetraisopropyl-ortho-titanate, peroxy-titanates, optionally formed in situ, etc.) and of silicon (like tetra-ethyl-ortho-silicate, silica sol, etc.).

The activation is in general performed by treating the catalyst with an aqueous solution of hydrogen peroxide, preferably containing also:

an amount of ammonia ($NH_3$) equal to or higher than 10 kg per 100 kg of solution; or 0.5 or more equivalents per liter of an acid with a pK value equal to or lower than 5 and in particular an inorganic acid selected from sulfuric acid, phosphoric acid, nitric acid and hydrogen chloride.

The hydrogen peroxide can also be present during the synthesis of the titanium silicalite from Si and Ti sources, but it is the final activation with hydrogen peroxide the true responsible for the increase in catalytic activity.

In the case of an usual hydrothermal synthesis of the titanium-silicalite, the temperature of the calcination preceeding the activation can be advantageously limited at 430° C. or at lower temperatures. The effectiveness of the activation is so high that quite satisfactory results are reached even limiting said thermal treatment (preceeding the activation) to a simple drying at 120°–130° C.; such a surprising fact allows to avoid the burdensome calcination which is usually carried out for decomposing the organic templating agent.

The ammoximation is in general performed in the liquid phase at 25°–150° C., but preferably at 40°–120° C. and, when the carbonylic compound is cyclohexanone, still better at 60°–120° C.; a test carried out at 15° C. yielded definitely unsatisfactory results. The reaction may be in general carried out at atmospheric pressure or, preferably, at a slightly higher pressure, in order to keep dissolved, in the reaction medium, a quantity of ammonia at least equal to that required by the synthesis. The catalyst may be used in form of a fixed bed or as a slurry (finely dispersed and suspended in the reaction medium) provided there be used reactors having surfaces that are compatible with the presence of hydrogen peroxide. Very satisfactory results were obtained using a trickle-bed reactor, whereinto ammonia was fed in the form of a gas.

In the case of a discontinuous process, it is advisable to use from 0.1 to 50 parts by weight (but preferably 1–20 parts) of pure catalysts, binder excluded, per 100 parts of ketone; in the case of a continuous process, it is advisable to use a space velocity from 0.1 to 200 kg/h of ketone per kg of pure catalyst. The $H_2O_2$:ketone molar ratio is in general from 0.3 to 2.5, but preferably from 0.5 to 1.5 (even better from 0.5 to 1.3), $H_2O_2$ to be intended as 100% pure hydrogen peroxide (dilution water excluded). The $NH_3$:ketone molar ratio must be equal to or greater than 1 (preferably 1.5), otherwise parallel disturbing reactions would take place. The reaction medium may consist of water or of water and an organic solvent like toluene, dioxane, cyclohexanol, t-amylic alcohol; quite exceptional results were obtained using as a solvent tertiary butyl alcohol, the t-butanol:ketone molar ratio being in general from 0.1 to 100.

At the end of the reaction the oximes may be separated in various ways, for instance by extraction with suitable solvents (such as: benzene, toluene or the same ketone used for the synthesis), whereby an organic hydrophobic phase and an aqueous phase are formed. The oxime and the unreacted torque are transferred into the organic layer; the aqueous layer, containing the $NH_3$ excess, as well as traces of ketone and oxime, may be conveniently recycled back to the reaction zone. Alternatively, the extraction may be carried out at the same time as the synthesis, operating in a biphasic system; such system may be advantageously realized by using a couple of solvents with different characteristics, for example t-butanol (hydrophile) and toluene (hydrophobic). When a continuous process is carried out, the same carbonylic compound is advantageously fed in admixture with the organic solvent, for instance t-butyl-alcohol; a trickle-bed reactor is quite suited for the ammoximation and an alternative is represented by a stirred reactor.

The enclosed figures are showing some aspects of the invention, without limiting however in any way the scope thereof.

Figure 1:
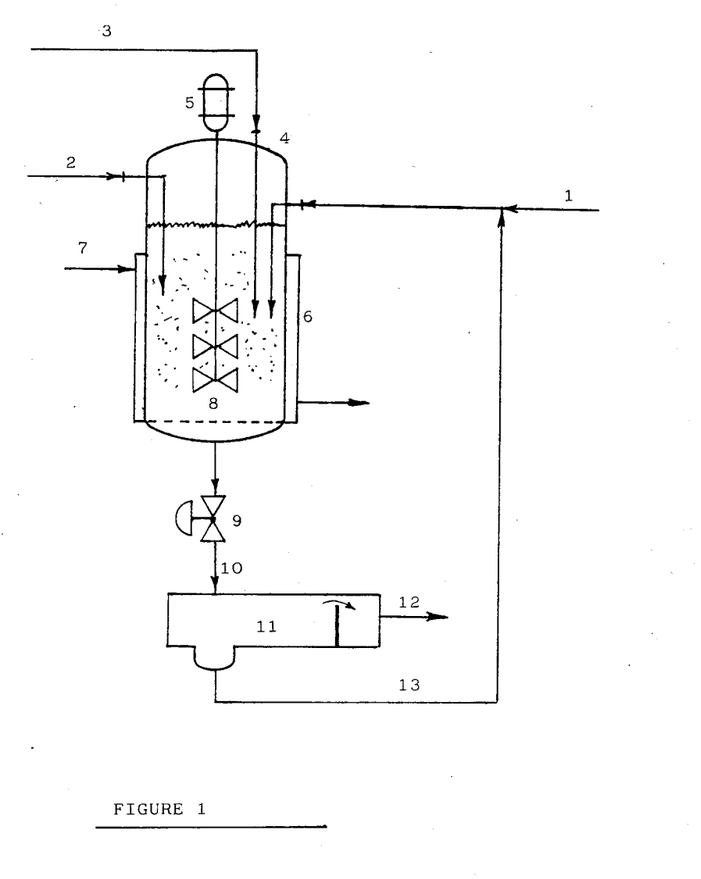
FIG. 1 is concerning a continuous ammoximation performed in an isothermal slurry reactor with a rotating stirrer.

According to FIG. 1, an aqueous solution of hydrogen peroxide (1), a solution of ketone (or aldehyde) in an organic solvent (2) and an aqueous solution (or a gaseous stream) of ammonia (3), are entering, by means of feed pipes immersed in the liquid reacting mixture, a reactor (4) provided with a blade-stirrer (5) and with a heating jacket (6), fed with a steam stream (7). A filtering plate (8) is retaining the catalyst particles (suspended in the reaction liquid) and an automatic valve (9) is controlling the liquid level and the flow rate of the effluent (10). An extraction device (11) allows then the separation (by means of a hydrophobic solvent not shown in FIG. 1) into an organic layer (12), which is transferred to further operations, and an aqueous layer (13), still containing the $NH_3$ excess and the last traces of carbonylic (non reacted) compound and of oxime, which can be advantageously recycled to the ammoximation reactor.

Figure 2:
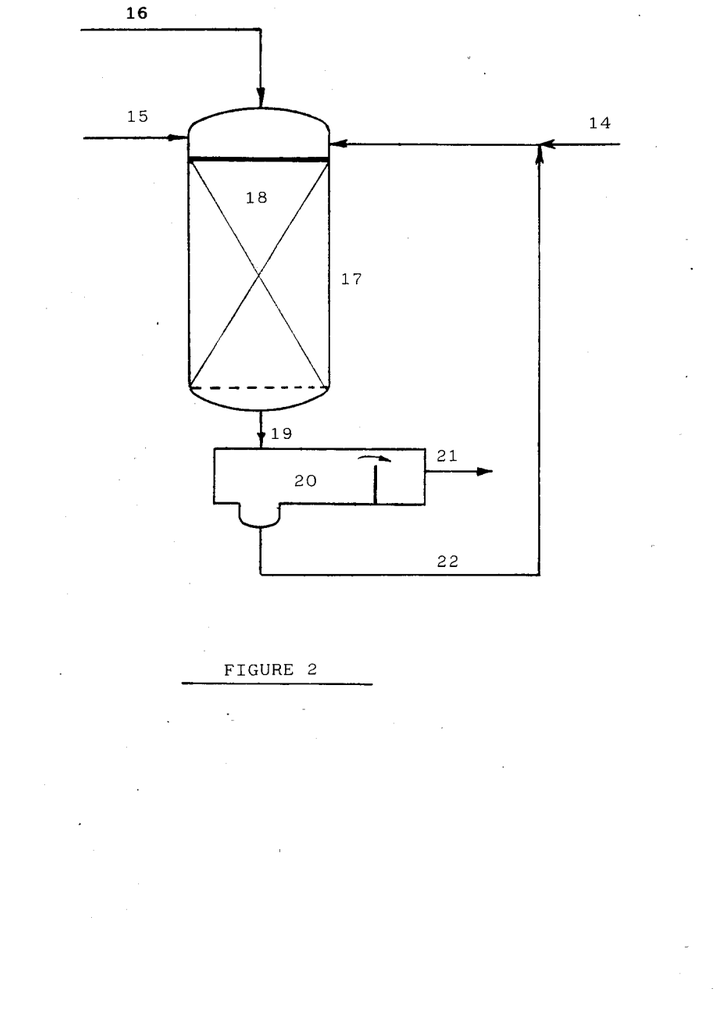
FIG. 2 is concerning a continuous ammoximation, performed in an adiabatic trickle-bed reactor.

Following FIG. 2, the aqueous solution of $H_2O_2$ (14), a pre-heated solution of carbonylic compound in an organic solvent (15) and a stream of pre-heated gaseous or aqueous ammonia (13) are injected into an adiabatic reactor (17) containing a bed of catalyst (18) in the form of pellets, granules and so on; the best results were reached by using catalyst extrudates, namely small cylinders of catalyst obtained by the extrusion. The effluent (19) is then entering the extraction device (20) which allows the separation into the two streams (21) and (22), which have the same meaning of the analogous streams on FIG. 1.

The following examples will further illustrate the invention, without, however, limiting in any way the scope of the inventon itself.

EXAMPLE 1

(preparation of the catalyst; blank test)

544 grams of tetraethyl orthosilicate were charged into a Pyrex glass (flame-resistant) flask, provided with a stirrer and kept under an inert atmosphere of nitrogen; thereupon 24 g of a tetraisopropyl titanate were added and, finally, there were added dropwise 1,200 g of an aqueous solution of tetrapropyl-ammonium hydroxide at 20% by weight concentration. The mixture was kept under stirring for 1 hour at room temperature, whereafter it was allowed to rest, still at room temperature, for another hour; the temperature was then gradually raised up to 78° C., in order to remove ethyl alcohol, and then brought up to 98° C., in order to remove isopropyl alcohol. The elimination of the alcohols, released by hydrolysis was carried out under stirring and took 5 hours. After cooling, the volume of the liquid was brought up to 2 liters by addition of de-ionized water and the resulting solution (homogeneous and opalescent) was transferred into an autoclave fitted with a stirrer, where a hydrothermal synthesis was performed at 175° C. over a stretch of 10 days, under autogenous pressure. At the end, after cooling, the synthesis mixture was filtered and the solid was washed until reaching neutral pH; thereafter it was dried at 120° C. for 15 hours and calcined at 550° C. for 6 hours.

EXAMPLE 2

(activation by $H_2O_2$ and $H_2SO_4$)

Example 1 was partially repeated up to the hydrothermal synthesis (10 days at 175° C.), whereafter the reaction mixture was cooled and filtered, and the solid product was washed for a long time, until reaching neutral pH; it was then dried at 120° C. for 15 hours and the dried product was calcined at 420° C. for 10 hours. The use of a much lower calcination temperature, with respect to that of Example 1, before the successive activating treatment with hydrogen peroxide and $H_2SO_4$ (see further on), proved to be very advantageous to the catalytic activity. The calcined product was placed into a beaker and mixed under stirring with an aqueous solution prepared from 100 cm$^3$ of $H_2O_2$ (30% by weight) and 1,000 cm$^3$ of diluted sulphuric acid (5% b.w.); this treatment, from now onward indicated as "activation", was carried out at 70° C. for 2 hours and the liquid was separated by decantation. The "activation" was repeated further two times, with a fresh solution, and after the last "activation" the solid was filtered and repeatedly washed with deionized water (untill neutral pH), whereafter the product was dried at 120° C. for 15 hours and calcined at 550° C. for 2 hours.

EXAMPLE 3

(synthesis of cyclohexanon-oxime; comparative test)

A glass reactor, fitted with a stirrer and a heating jacket, was preliminarily pressurized with an inert gas (nitrogen). There were loaded 1.5 g of a fine powder, obtained by grinding the titanium-silicalite prepared according to example 1 (average diameter of the particle equal to or less than 5 micrometers); thereafter 50 g of water and 4 g of ammonia (0.24 moles) were added. The whole was then vigorously stirred and 9.5 g of cyclohexanone (0.1 moles) were added. The temperature was gradually raised by feeding into the jacket of the reactor a thermostatic fluid. After 30 minutes the internal temperature of the reactor attained 80° C., while the pressure rised slightly above atmospheric pressure; at this point the addition of $H_2O_2$ (aqueous solution at 30% b.w). was started, using a metering pump, and carried on for 5 hours; globally, there were fed 12.46 g of $H_2O_2$ (0.11 moles). During the addition of $H_2O_2$ a pressure drop was noted inside the reactor. At the end, after cooling, ethylether was added to the suspension inside the reactor; after stirring for a few minutes, the liquid was separated from the catalyst by filtering. The aqueous and the organic phases were separated (through a separatory funnel) and the gas-chromatographic analysis showed a 45% ketone conversion and a corresponding 35% selectivity to oxime, but 78% of the $H_2O_2$ was lost by decomposition, while the oxime yield (referred to $H_2O_2$) amounted to 15% only.

EXAMPLE 4

(synthesis of cyclohexanon-oxime according to the invention)

Example 3 was repeated, replacing the scarcely active catalyst of the first example with the catalyst of example 2, activated by $H_2O_2$ and $H_2SO_4$; the results were incomparably better, and more precisely:

| | |
|---|---|
| cyclohexanone conversion | 87.0% |
| selectivity to cyclohexanone-oxime (based on the cyclohexanone conversion) | 81.0% |
| hydrogen peroxide conversion | 93.5% |
| $H_2O_2$ lost by decomposition | 22.0% |
| oxime yield (referred to the ketone) | 70.5% |
| oxime yield (referred to hydrogen peroxide) | 71.5% |

EXAMPLE 5

(addition of t-butyl alcohol)

Example 4 was repeated, replacing 25 cm³ of water by 25 cm³ of t-butyl alcohol. Moreover, the amounts of ketone (10.185 g=0.104 moles) and of total $H_2O_2$ (11.55 g=0.107 moles) were slightly modified; the results, quite exceptional and surprising in an absolute sense (see Table 1), differ in a determining way above all the results of the Prior Art.

EXAMPLE 6

Example 5 was repeated, modifying slightly the amount of ketone (9.87 g=0.1 mole) and of total $H_2O_2$ (10.14 g=0.094 moles), thereby obtaining the results recorded on Table 1.

TABLE 1

| EXAMPLE | Ex. 3 (*) | Ex. 4 | Ex. 5 | Ex. 6 |
|---|---|---|---|---|
| Catalyst | from Ex. 1 | from Ex. 2 | from Ex. 2 | from Ex. 2 |
| Ketone conversion | 45.3% | 87.0% | 100.0% | 89.6% |
| Selectivity to oxime (with respect to converted ketone) | 35.0% | 81.0% | 92.2% | 96.0% |
| $H_2O_2$ conversion | 93.1% | 93.5% | 95.1% | 97.2% |
| $H_2O_2$ loss | 78.1% | 22.0% | 6.0% | 5.4% |
| Oxime yield (referred to $H_2O_2$) | 15.0% | 71.5% | 89.1% | 91.7% |

(*) comparative test

EXAMPLE 7 and 8

Example 4 was repeated replacing in one case 25 cm³ of $H_2O$ by 25 cm³ of dioxane (thus obtaining a homogenous liquid phase) and in the other case by 25 cm³ of toluene (thus obtaining 2 liquid phases); the results are recorded on Table 2.

EXAMPLE 9

Example 5 was repeated adding to the (water+t-butanol) mixture also 25 cm³ of toluene, thus obtaining 2 liquid phases; results are recorded on Table 2.

TABLE 2

| EXAMPLES | Ex. 7 | Ex. 8 | Ex. 9 |
|---|---|---|---|
| Solvent | Dioxane | Toluene | Toluene + Alcohol |
| Ketone conversion | 93.7% | 86.1% | 96.3% |
| Selectivity to oxime (based on the ketone conversion) | 86.8% | 87.1% | 89.3% |
| $H_2O_2$ conversion | 96.6% | 92.5% | 97.1% |
| $H_2O_2$ loss | 23.3% | 22.2% | *0.6% |
| Oxime yield (referred to $H_2O_2$) | 73.3% | 70.3% | 96.5% |

EXAMPLE 10 and 11

Example 5 was repeated varying the temperature of the reaction mixture. Results are recorded in Table 3.

TABLE 3

| EXAMPLE | 10 | 11 |
|---|---|---|
| TEMPERATURE | 60° C. | 70° C. |
| Ketone conversion | 81.5% | 90.2% |
| Selectivity to oxime (based on the ketone conversion) | 87.1% | 96.4% |
| $H_2O_2$ conversion | 95.3% | 95.8% |
| $H_2O_2$ loss | 18.9% | 6.4% |
| Oxime yield (referred to $H_2O_2$) | 76.4% | 89.4% |

EXAMPLES 12–14

Example 5 was repeated, varying the amount of catalyst suspended in the reaction mixture and the feeding time of $H_2O_2$; the results are recorded on Table 4.

TABLE 4

| EXAMPLES | Ex. 12 | Ex. 13 | Ex. 14 |
|---|---|---|---|
| Feeding time of $H_2O_2$ | 2.5 h | 5 h | 2.5 h |
| Catalyst concentration | 15 g/l | 30 g/l | 30 g/l |
| Ketone conversion | 72.5% | 89.6% | 92.4% |
| Selectivity to oxime (based on the ketone conversion) | 95.9% | 96.0% | 94.5% |
| $H_2O_2$ conversion | 92.0% | 97.2% | 96.6% |
| $H_2O_2$ loss | 14.2% | 5.4% | 5.2% |
| Oxime yield (referred to $H_2O_2$) | 77.9% | 91.7% | 91.4% |

EXAMPLE 15

Example 5 was repeated, modifying the way in which the reactants were fed to the reactor. Cyclohexanone and $H_2O_2$ were contemporarily added through different metering pumps to the suspension of the catalyst in the liquid mixture of t-butyl alcohol and aqueous ammonia. The obtained results were:

| | |
|---|---|
| ketone conversion = | 91.4% |
| selectivity to oxime (based on the ketone conversion) = | 100% |
| hydrogen peroxide conversion = | 100% |
| oxime yield (referred to $H_2O_2$) = | 99.4% |

EXAMPLE 16

(catalyst preparation in the presence of hydrogen peroxide)

15 g of tetraethylortho-titanate were dropwise added to 250 cm³ of de-ionized $H_2O$, under stirring, thereby causing the hydrolysis of the titanate. The resulting white and jellylike suspension was cooled to 5° C. by means of a cooling bath ($H_2O$+ice) and 180 cm³ of $H_2O_2$, previously cooled to 5° C., were dropwise added under stirring. The stirring was maintained for further 2 hours at such low temperature. A perfectly clear and orange solution was thus obtained; thereupon, there were added 300 cm³ of a 20% aqueous solution of tetrapropylammonium hydroxide, previously cooled down to 5° C., After 1 hour under stirring, 50 g of a silica sol (trade name KETJEN SOL AS 40) were added and vigorously mixed. The suspension was allowed to rest overnight, whereafter it was slowly heated up to 78° C. and kept at this temperature for 6 hours; it was then transferred into an autoclave and submitted to hydrothermal synthesis at 175° C. for six days, under autogenous pressure. At the end, after cooling, the resulting mixture was filtered and the solid product was washed until neutral pH and dried at 120° C. for 15 hours. Part of the catalyst was then subjected to the same treatment as described in example 2, which consisted of: a calcination at 420° C. for 10 hours, an "activation" with $H_2O_2$ and $H_2SO_4$, a subsequent drying at 120° C. (for 15 h) and a final calcination at 550° C. (for 2 hours); the thus treated portion of catalyst ("H" portion) was used in the test of example 17. The remaining catalyst ("K" portion) was directly calcined at 550° C. (for 10 h), without any activation by $H_2O_2$ and $H_2SO_4$; such "K" portion was tested in example 18.

EXAMPLE 17

Example 5 was repeated, using the 'H' portion of the catalyst (prepared in the presence of $H_2O_2$ and mentioned in example 16) that is the portion post-treated with the "activation", according to the invention and based on $H_2O_2$ and $H_2SO_4$. The results are recorded on Table 5.

EXAMPLE 18

(comparative)

Example 17 was repeated, replacing the "H" portion of the catalyst by the "K" portion, that is, the part of catalyst that did not undergo said activation with $H_2O_2$ and $H_2SO_4$. The very poor results reported in Table 5 show quite clearly how critical the "activation" proves to be even in those cases in which hydrogen peroxide is already present as a reactant, during the titanium-silicalite synthesis.

TABLE 5

| EXAMPLE | 17 | 18 (*) |
|---|---|---|
| Catalyst (from Ex. 16) | "H" portion | "K" portion |
| Ketone conversion | 91.1% | 49.8% |
| Selectivity to oxime (based on the ketone conversion) | 89.8% | 83.6% |
| $H_2O_2$ conversion | 97.4% | 96.5% |
| $H_2O_2$ loss | 5.4% | 51.3% |
| Oxime yield (referred to $H_2O_2$) | 92.0% | 45.2% |

(*) Comparative

EXAMPLE 19

(preparation of the catalyst without calcination before the activation)

455 grams of tetraethyl orthosilicate were loaded into the flask of example 1, under nitrogen atmosphere, and 15 g of tetraethyl ortho-titanate were added; then, there were added dropwise 1,000 g of an aqueous solution of tetrapropyl-ammonium hydroxide at 20% by weight concentration. The resulting solution was kept under stirring for 1 hour at room temperature, whereafter it was allowed to rest, still at room temperature, for another hour; the temperature was then gradually raised up to 78° C. in order to remove ethyl alcohol; the elimination of the alcohol, released by hydrolysis, was carried out under stirring and took 5 hours. After cooling, the volume of the liquid was brought up to 2 liters by addition of deionized water and the resulting solution (homogeneous and opalescent) was transferred into an autoclave fitted with a stirrer, where the hydrothermal synthesis was performed at 175° C. over a stretch of 10 days, under autogenous pressure. At the end, after cooling, the synthesis mixture was filtered and the solid product was washed until reaching neutral pH; thereafter it was dried at 120° C. for 15 hours.

11.5 g of the thus dried product were placed into a beaker and mixed under stirring together with an aqueous solution prepared from 23 $cm^3$ of hydrogen peroxide (30% by weight) and 220 $cm^3$ of diluted sulphuric acid (5% bw); the activation was carried out at 70° C. for 2 hours and then the liquid was separated by decantation. The operation was repeated twice again with a fresh solution; after the last activation, the solid was filtered and repeatedly washed with de-ionized water (until neutral pH), whereafter the product was dried at 120° C. for 15 hours and calcined at 550° C. for 2 hours. The choice of a temperature much lower than that of example 1, before the successive activation with hydrogen peroxide and $H_2SO_4$, proved to be very advantageous for the catalytic activity. (see example 20).

EXAMPLE 20

1.52 g of the fine powder obtained by grinding the catalyst prepared according to example 19 (average diameter equal to or lower than 5 micrometers) were loaded into the reactor of example 3. Thereafter, 25 g of ter-butyl-alcohol, 21 g of water, 4 g (0.24 moles) of ammonia and 10.27 g (0.105 moles) of cyclohexanone were added. The temperature was gradually raised up to 80° C., by feeding into the reactor jacket a thermostatic fluid; during the heating the reactor's pressure rised slightly above the atmospheric level. At this temperatue, 10 g (0.093 moles) of $H_2O_2$ (aqueous solution at 31.6% b.w.) were fed, through a metering pump, over a stretch of 5 h, under vigorous stirring, and during the addition a pressure drop was noted inside the reactor. At the end, after cooling, ethyl ether was added to the suspension; after stirring for a few minutes, the liquid was separated from the catalyst by filtering. The aqueous and organic phase were separated (through a separatory funnel) and the gas-chromatographic analysis showed a 84.7% ketone conversion and a corresponding 99.8% selectivity to oxime; 1% of the $H_2O_2$ was lost by decomposition, and the oxime yield (referred to $H_2O_2$) was 95.2%.

EXAMPLE 21

Example 19 was repeated up to the hydrothermal synthesis (at 175° C. for 10 days) and to the subsequent drying at 120° C. for 15 hours. The thus obtained product was then calcined at 430° C. for 10 hours and the activation went on as pointed out in example 19.

EXAMPLE 22

Example 20 was repeated replacing the catalyst of example 19 by the catalyst of example 21, the experimental conditions being substantially identical to the ones of example 20; amounts of reactants and results are recorded on Table 6.

EXAMPLE 23

(activation by $H_2O_2$ and HCl)

Example 21 was repeated replacing the sulphuric acid by 220 $cm^3$ of diluted hydrochloric acid (at 2% by weight concentration).

EXAMPLE 24

Example 20 was repeated replacing the catalyst of example 19 by the catalyst of example 23, the experimental conditions being substantially identical to the ones of example 20; amounts of reactants and results are recorded on Table 6.

EXAMPLE 25

(activation by $H_2O_2$ and $H_3PO_4$)

Example 21 was repeated replacing the sulphuric acid by 220 cm$^3$ of diluted phosphoric acid (at 5% by weight concentration).

EXAMPLE 26

Example 20 was repeated replacing the catalyst of example 19 by the catalyst prepared according to example 25, the experimental conditions being substantially identical to the ones of example 20; amounts of reactants and results are recorded on Table 6.

TABLE 6

| EXAMPLES (*) | 20 | 22 | 24 | 26 |
|---|---|---|---|---|
| Catalyst from | Ex. 19 | Ex. 21 | Ex. 23 | Ex. 25 |
| Thermal treatment (**) | 120° C. | 430° C. | 430° C. | 430° C. |
| Activation by $H_2O_2$ and: | $H_2SO_4$ | $H_2SO_4$ | HCl | $H_3PO_4$ |
| Ketone (moles) | 0.105 | 0.103 | 0.102 | 0.103 |
| $H_2O_2$ (moles) | 0.093 | 0.094 | 0.096 | 0.095 |
| Ketone conversion | 84.7% | 92.1% | 96.2% | 91.3% |
| Selectivity to oxime | 99.8% | 91.6% | 91.0% | 88.2% |
| (based on the ketone conversion) | | | | |
| $H_2O_2$ conversion | 96.2% | 96.6% | 96.7% | 95.5% |
| $H_2O_2$ loss | 1.0% | 3.8% | 3.5% | 7.7% |
| Oxime yield (referred to $H_2O_2$) | 95.2% | 92.8% | 93.2% | 87.8% |

(*) titanium source = tetraethyl-titanate
(**) before activation

EXAMPLE 27

(synthesis of acetonoxime)

1.5 g of the fine powder obtained by grinding of the catalyst prepared according to example 21 (average diameter equal to or lower than 5 micrometers) were loaded into the reactor of example 3. Thereafter, 25 g of t-butyl-alcohol, 21 g of water, 4 g (0.24 moles) of ammonia and 5.8 g (0.1 moles) of acetone were added while stirring. The temperature was raised up to 80° C. and 11.6 g (0.10 moles) of an aqueous solution of hydrogen peroxide (30% by weight) were fed over a stretch of 5 hours. The suspension was cooled and the catalyst was separated by filtration; the gas-chromatographic analysis showed a 91.3% conversion of acetone and a 78.6% selectivity to oxime (based on the ketone conversion); the oxime yield was 70.1% referred to $H_2O_2$ and 20.5% of $H_2O_2$ was lost by decomposition.

EXAMPLE 28

(synthesis of butanonoxime)

Example 27 was repeated replacing acetone by 7.52 g (0.104 moles) of methyl-ethyl-ketone (butan-2-one) and feeding 10.0 g (0.09 moles) of $H_2O_2$ (31.6% w). Data and results are recorded on Table 7.

EXAMPLE 29

(synthesis of acetophenonoxime)

Example 27 was repeated replacing acetone by acetophenone (11.9 g; 0.099 moles) and modifying the solvent amount (12 g of water and 37 g of t-butyl alcohol). Data and results are recorded on Table 7.

EXAMPLE 30

(synthesis of benzaldoxime)

Example 29 was repeated replacing acetophenone by 10.67 g of benzaldehyde (0.107 moles). Data and results are recorded on Table 7.

EXAMPLE 31

(synthesis of heptanaloxime)

Example 29 was repeated replacing acetophenone by 2.35 g (0.02 moles) of heptanal and lowering the amounts of hydrogen peroxide (2.18 g of 27.41% b.w. aqueous solution, namely 0.018 moles of 100% product). Data and results are recorded on Table 7.

TABLE 7

| EXAMPLE | Ex. 27 | Ex. 28 | Ex. 29 | Ex. 30 | Ex. 31 |
|---|---|---|---|---|---|
| AMMOXIMATION OF: | Acetone | Butan-2-one | Acetophenone | Benzaldehyde | Heptanal |
| Carbonylic compound (moles) | 0.100 | 0.104 | 0.099 | 0.107 | 0.020 |
| $H_2O_2$ (moles) | 0.100 | 0.090 | 0.090 | 0.090 | 0.018 |
| Results: | | | | | |
| Carbonylic compound conversion | 91.3 | 85.6 | 50.8 | 100.0 | 78.7 |
| Selectivity to oxime (based on the carbonilyc compound conversion) | 78.6 | 88.3 | 98.1 | 83.1 | 69.4 |
| $H_2O_2$ conversion | 90.6 | 95.6 | 97.2 | 98.8 | 95.4 |
| $H_2O_2$ loss | 20.5 | 11.6 | 48.3 | 18.0 | 36.0 |
| Oxime yield (referred to $H_2O_2$) | 70.1 | 85.0 | 48.9 | 80.8 | 63.9 |

EXAMPLE 32

(continuous process for the manufacture of cyclohexanon-oxime)

16.9 g of the catalyst prepared according to example 19 were loaded into a cylindrical glass reactor, provided with a rotating stirrer and a filtering plate on the bottom (see FIG. 1); the following streams were fed to the reactor:

| | |
|---|---|
| cyclohexanone | 44 g (h)$^{-1}$, i.e. 0.449 moles (h)$^{-1}$ |
| $H_2O_2$ (27% b.w.) | 70 g (h)$^{-1}$, i.e. 0.555 moles (h)$^{-1}$ |
| $NH_3$ (gaseous) | 15.4 g (h)$^{-1}$, i e. 0.906 moles (h)$^{-1}$ |
| t-butyl-alcohol | 91 g (h)$^{-1}$ |
| water | 76 g (h)$^{-1}$ |

The outlet flow rate was controlled to keep a reaction volume of 800 cm$^3$; a thermostatic fluid maintained the temperature at 83° C., while the pressure was 2 bar. After 8 hours the gas-chromatograhic analysis was showing a quantitative conversion of the ketone and a ketone-to-oxime selectivity equal to 94.1%; after 28 hours the same conversion was 99,9% and said selectivity was 98.4%, what is corresponding to a 98.3% global yield.

EXAMPLE 33

(trickle-bed)

The titanium-silicalite prepared according to example 19 was ground (average diameter of the powder particles=5 micrometers) and kneaded with deionized water and 10% by weight of bentonite; the paste was extruded, dried at 120° C. for 12 hours and calcined at 550° C. for two hours. 2 g of extruded catalyst were loaded into a reactor kept at 80° C. and fed from the top (see FIG. 2) with:

---
1.9 cm³/h of a solution containing 23.73% by weight of cyclohexanone and 76.27% by weight of t-butyl-alcohol;
0.33 cm³/h of aqueous $H_2O_2$ at 27% by weight concentration;
0.25 liters/h of gaseous $NH_3$.
---

After 30 hours the ketone conversion was 72.9% and the corresponding selectivity to oxime was 93.2%.

EXAMPLE 34

(Activation by $H_2O_2$)

Example 19 was repeated replacing the $H_2O_2+H_2SO_4$ mixture by $H_2O_2$ (300 cm³ of an aqueous solution at 30% b.w. concentration).

EXAMPLE 35

Example 20 was repeated replacing the catalyst of example 19 by the catalyst of example 34, the experimental conditions being substantially identical to the ones of example 20. The gas-chromatographic analysis showed a 75.1% ketone conversion and a corresponding 91.9% selectivity to oxime; 18.9% of the $H_2O_2$ was lost by decomposition and the oxime yield (referred to $H_2O_2$) was 76.2%.

EXAMPLE 36

Example 19 was repeated up to the hydrothermal synthesis (at 175° C. for 10 days) and to the subsequent drying at 120° C. for 15 hours. The thus obtained product was then calcined at 430° C. for 10 hours and the activation went on as in example 35.

EXAMPLE 37

Example 20 was repeated replacing the catalyst of example 19 by the catalyst of example 36, the experimental conditions being substantially identical to the ones of example 20; amounts of reactants and results are recorded on Table 8.

EXAMPLE 38

(activation by $H_2O_2$ and $NH_3$)

Example 19 was repeated up to the hydrothermal synthesis (at 175° C. for 10 days) and to the subsequent drying at 120° C. for 15 hours. The thus obtained product was then calcined at 430° C. or 10 hours. 11.5 g of the thus dried product were suspended into 290 cm³ of aqueous ammonia (at a 15% by weight concentration). At this point, 130 cm³ of $H_2O_2$ (30% b.w.) were added gradually under stirring (0.4 cm³/minute). This activation was carried out at 70° C. for 2 hours and then the liquid was separated by decantation. The operations were then continued as in example 19.

EXAMPLE 39

Example 20 was repeated replacing the catalyst of example 19 by the catalyst of example 38, the experimental conditions being substantially identical to the ones of example 20; amounts of reactants and results are recorded on Table 8.

TABLE 8

| EXAMPLE (*) | 35 | 37 | 39 |
|---|---|---|---|
| Catalyst from | Ex. 34 | Ex. 36 | Ex. 38 |
| Thermal treatment(**) | 120° C. | 430° C. | 430° C. |
| Activation by: | $H_2O_2$ | $H_2O_2$ | $H_2O_2 + NH_3$ |
| Ketone (moles) | 0.103 | 0.102 | 0.101 |
| $H_2O_2$ (moles) | 0.094 | 0.095 | 0.097 |
| Ketone conversion | 75.1% | 92.8% | 89.5% |
| Selectivity to oxime (based on ketone conversion) | 91.9% | 88.4% | 94.0% |
| $H_2O_2$ conversion | 95.0% | 94.7% | 94.2% |
| $H_2O_2$ loss | 18.9% | 7.0% | 6.2% |
| Oxime yield (based on $H_2O_2$) | 76.2% | 87.7% | 88.0% |

(*) titanium source = tetraethyl-ortho-titanate
(**) before activation

EXAMPLE 40 and 41

(Trickle bed)

Example 33 was repeated feeding together, as sole solution, the ketonic solution and the hydrogen peroxide solution of same example 33. Moreover, the operative conditions were changed as follows:

| | EX. 40 | EX. 41 |
|---|---|---|
| catalyst (from ex. 19) | 8 g | 8 g |
| feed rate: | 30 cm³/h | 60 cm³/h |
| feed composition (% by weight): | | |
| ketone | 4.30 | 8.09 |
| t-butyl-alchol | 44.68 | 40.89 |
| hydrogen peroxide | 1.44 | 2.64 |
| water | 49.58 | 48.38 |
| (gaseous) ammonia: | 0.5 lt/h | 2.0 lt/h |
| After a 70 hour run, the results were as follows: | | |
| Cyclohexanone conversion | 76.2% | 65.7% |
| Corresponding selectivity to oxime | 99.7% | 95.2% |
| Oxime yield (based on hydrogen peroxide) | 78.9% | 66.6% |

What is claimed is:

1. A continuous catalytic process for the manufacture of cyclohexanone-oxime by ammoximation in the liquid phase of cyclohexanone with $NH_3$ and $H_2O_2$, wherein:
    the catalyst is a titanium-silicalite (with a Si:Ti atomic ratio at least equal to 30), subjected, before use, to an activation with $H_2O_2$ and optionally also with $H_2S_4$;
    the ammoximation is carried out at 60°–120° C., in the presence of t-butanol (and/or cyclohexanol) according to a ketone:$H_2O_2$ molar ratio from 0.5 to 1.3, according to $NH_3$:ketone molar ratios equal to or greater than 1.5 and according to t-butanol (and/or cyclohexanol): ketone molar ratios from 0.1 to 100 (but preferably from 0.5 to 10);
    the ketone is fed into the ammoximation zone in admixture with t-butanol (and or cyclohexanol), the amount of ketone being from 2 to 200 kg/h per kg of pure titanium silicalite.

2. A process according to claim 1, wherein the ammoximation is carried out in the presence of a solvent immiscible with water and at any rate less hydrophile (that is, more hydrophobic) than the tertiary butyl alcohol (and/or cyclohexanol), whereby the ammoximation takes place in a biphasic system.

3. A process according to claim 1, wherein the ammoximation is continuously carried out in a stirred slurry reactor.

4. A process according to claim 1, wherein the reactants are continuously fed into a trickle-bed reactor.

5. A process according to claim 3 or to claim 27, wherein ammonia is fed as a gas.

6. A catalytic process for the manufacture of oximes by reaction, in the liquid phase, of the corresponding carbonylic compounds with ammonia and hydrogen peroxide, the catalyst being titanium-silicalite, characterized in that the catalyst is subjected before use to an activating treatment with an aqueous solution of hydrogen peroxide, after which the treated catalyst is dried and calcined.

7. A process according to claim 6, wherein said activating treatment is carried out in the presence of at least 0.5 equivalent per liter of solution of an acid showing a pK value equal to or lower than 5.

8. A process according to claim 7, wherein said acid is selected from the class consisting of sulphuric acid, phosphoric acid, nitric acid, and hydrogen chloride.

9. A process according to claim 6, wherein said aqueous solution contains also at least 10 parts by weight of ammonia per 100 parts of solution.

10. A process according to any one of claims 6 to 9, wherein the amount of pure catalyst, binder excluded, is from 1 to 500 g per kg of carbonylic compound.

11. A process according to any one of claims 6 to 9, wherein the catalyst is in admixture with an inert binder.

12. A process according to any one of claims 6 to 9, wherein the Si:Ti atomic ratio, inside the titanium silicalite, is at least 30.

13. A process according to any one of claims 6 to 9, wherein hydrogen peroxide is also present during the preparation of the titanium-silicalite.

14. A process according to any one of claims 6 to 9, wherein the titanium-silicalite is manufactured by hydrothermal synthesis and wherein the thus-manufactured titanium-silicalite is submitted, before activation, to a thermal treatment at a temperature equal to or lower than 430° C.

15. A process according to claim 14, wherein the thermal treatment temperature is equal to or lower than 130° C.

16. A process according to any one of claims 6 to 9, wherein said carbonyl compound is selected from the class consisting of cyclohexanone, acetone, methyl-ethyl-ketone, acetophenone, cyclododecanone, enanthic aldehyde, and benzaldedhyde.

17. A process according to claim 16, wherein said carbonyl compound is cyclohexanone.

18. A process according to any one of claims 6 to 9, wherein the ammoximation temperature is from 25° to 150° C., the pressure being equal to or greater than atmospheric pressure.

19. A process according to any one of claims 6 to 9, wherein the $NH_3$: carbonyl compound molar ratio is equal to or greater than 1, and the ammoximation temperature is from 40° to 120° C.

20. A process according to any one of claims 6 to 9, wherein the $NH_3$: carbonyl compound molar ratio is equal to or greater than 1.5, and the ammoximation temperature is from 60° to 120° C.

21. A process according to any one of claims 6 to 9, wherein the ammoximaton is performed in water.

22. A process according to claim 21, wherein the ammoximation is performed in water and in an organic solvent.

23. A process according to claim 21, wherein the ammoximation is performed in water and in tertiary butyl alcohol and/or cyclohexanol, optionally in admixture with dioxane or toluene.

24. A process according to claim 21, wherein the ammoximation is performed in the presence of a couple of solvents, one of said solvents being less hydrophylic than the other.

25. A process according to claim 24, wherein said solvents consist of t-butanol and/or cyclohexanol and toluene.

26. A process according to any one of claims 6 to 9, wherein the ammoximation feed ratio:

$$\frac{(100\%) \text{ hydrogen peroxide}}{\text{carbonyl compound}}$$

is from 0.3 to 2.5 by moles.

27. A process according to claim 26, wherein said ratio is from 0.5 to 1.5.

28. A process according to claim 26, wherein said ratio is from 0.5 to 1.3.

29. A process according to any of claims 6 to 9, wherein the ammoximation is carried out in a continuous manner, the space velocity being from 0.1 to 200 kg/h of carbonyl compound per kg of pure titanium-silicalite, binder excluded.

30. A process according to any one of claims 6 to 9, wherein the carbonyl compound is continuously fed into the reaction zone in admixture with tertiary-butanol and/or cyclohexanol.

31. A process according to any one of claims 6 to 9, wherein the ammonia required by ammoximation is fed in a form selected from the gaseous form and an aqueous solution.

* * * * *

UNITED STATES PATENT AND TRADEMARK OFFICE
CERTIFICATE OF CORRECTION

PATENT NO. : 4,794,198
DATED : December 27, 1988
INVENTOR(S) : ROFFIA et al.

It is certified that error appears in the above-identified patent and that said Letters Patent is hereby corrected as shown below:

Column 2, line 54, change "torque" to --Ketone--.

Column 8, line 30, change "tue" to --ture--.

Column 12, line 57, change "$H_2S_4$" to --$H_2SO_4$--.

Signed and Sealed this

Nineteenth Day of September, 1989

Attest:

DONALD J. QUIGG

Attesting Officer

Commissioner of Patents and Trademarks